US010245102B2

(12) United States Patent
Payne et al.

(10) Patent No.: US 10,245,102 B2
(45) Date of Patent: *Apr. 2, 2019

(54) ELECTROSURGICAL INSTRUMENT INCLUDING AN ADHESIVE APPLICATOR ASSEMBLY

(71) Applicant: COVIDIEN LP, Mansfield, MA (US)

(72) Inventors: Kellie F. Payne, Rock Hill, SC (US); William H. Nau, Jr., Longmont, CO (US); Duane E. Kerr, Loveland, CO (US)

(73) Assignee: COVIDIEN LP, Mansfield, MA (US)

( * ) Notice: Subject to any disclaimer, the term of this patent is extended or adjusted under 35 U.S.C. 154(b) by 247 days.

This patent is subject to a terminal disclaimer.

(21) Appl. No.: 15/194,886

(22) Filed: Jun. 28, 2016

(65) Prior Publication Data

US 2016/0302855 A1 Oct. 20, 2016

Related U.S. Application Data

(63) Continuation of application No. 14/054,173, filed on Oct. 15, 2013, now Pat. No. 9,375,259.

(Continued)

(51) Int. Cl.
*A61B 18/14* (2006.01)
*A61B 18/00* (2006.01)

(52) U.S. Cl.
CPC ...... *A61B 18/1445* (2013.01); *A61B 18/1477* (2013.01); *A61B 2018/0063* (2013.01);
(Continued)

(58) Field of Classification Search
CPC .......... A61B 18/1445; A61B 2018/143; A61B 2018/1467; A61B 2018/1455;
(Continued)

(56) References Cited

U.S. PATENT DOCUMENTS

D249,549 S    9/1978 Pike
D263,020 S    2/1982 Rau, III
(Continued)

FOREIGN PATENT DOCUMENTS

CN    201299462 Y    9/2009
DE    2415263 A1    10/1975
(Continued)

OTHER PUBLICATIONS

U.S. Appl. No. 08/926,869, filed Sep. 10, 1997, James G. Chandler.
(Continued)

*Primary Examiner* — Eun Hwa Kim

(57) ABSTRACT

The surgical instrument for sealing and/or cutting tissue includes a handle assembly and an end effector assembly operatively connected to the handle assembly. The end effector assembly includes first and second jaw members each including a jaw housing and an electrically conductive surface defining a plurality of bores and an adhesive applicator assembly disposed in one of the jaw members. The electrically conductive surfaces are configured to effect a tissue seal. The adhesive applicator assembly includes a platform defining a reservoir therein and a plurality of needles in communication with the reservoir. The platform is movable between a neutral position in which the plurality of needles are disposed within the jaw housing and an actuated position in which the plurality of needles extend through the respective plurality of bores defined in the electrically conductive surface.

14 Claims, 9 Drawing Sheets

Related U.S. Application Data

(60) Provisional application No. 61/718,067, filed on Oct. 24, 2012.

(52) U.S. Cl.
CPC .............. *A61B 2018/00083* (2013.01); *A61B 2018/00601* (2013.01); *A61B 2018/143* (2013.01); *A61B 2018/1455* (2013.01); *A61B 2018/1467* (2013.01)

(58) Field of Classification Search
CPC .. A61B 2018/0063; A61B 2018/00083; A61B 2018/1477; A61B 2018/00601
See application file for complete search history.

(56) References Cited

U.S. PATENT DOCUMENTS

| | | | |
|---|---|---|---|
| 4,392,493 A | 7/1983 | Niemeijer | |
| D295,893 S | 5/1988 | Sharkany et al. | |
| D295,894 S | 5/1988 | Sharkany et al. | |
| D298,353 S | 11/1988 | Manno | |
| D299,413 S | 1/1989 | DeCarolis | |
| D343,453 S | 1/1994 | Noda | |
| D348,930 S | 7/1994 | Olson | |
| D349,341 S | 8/1994 | Lichtman et al. | |
| D354,564 S | 1/1995 | Medema | |
| D358,887 S | 5/1995 | Feinberg | |
| 5,571,216 A * | 11/1996 | Anderson | A61B 17/00491 128/898 |
| D384,413 S | 9/1997 | Zlock et al. | |
| H1745 H | 4/1998 | Paraschac | |
| D402,028 S | 12/1998 | Grimm et al. | |
| D408,018 S | 4/1999 | McNaughton | |
| D416,089 S | 11/1999 | Barton et al. | |
| D424,694 S | 5/2000 | Tetzlaff et al. | |
| D425,201 S | 5/2000 | Tetzlaff et al. | |
| H1904 H | 10/2000 | Yates et al. | |
| D449,886 S | 10/2001 | Tetzlaff et al. | |
| D453,923 S | 2/2002 | Olson | |
| D454,951 S | 3/2002 | Bon | |
| D457,958 S | 5/2002 | Dycus et al. | |
| D457,959 S | 5/2002 | Tetzlaff et al. | |
| H2037 H | 7/2002 | Yates et al. | |
| 6,443,952 B1 | 9/2002 | Muller et al. | |
| D465,281 S | 11/2002 | Lang | |
| D466,209 S | 11/2002 | Bon | |
| D493,888 S | 8/2004 | Reschke | |
| D496,997 S | 10/2004 | Dycus et al. | |
| D499,181 S | 11/2004 | Dycus et al. | |
| D502,994 S | 3/2005 | Blake, III | |
| D509,297 S | 9/2005 | Wells | |
| D525,361 S | 7/2006 | Hushka | |
| D531,311 S | 10/2006 | Guerra et al. | |
| D533,274 S | 12/2006 | Visconti et al. | |
| D533,942 S | 12/2006 | Kerr et al. | |
| D535,027 S | 1/2007 | James et al. | |
| D538,932 S | 3/2007 | Malik | |
| D541,418 S | 4/2007 | Schechter et al. | |
| D541,611 S | 5/2007 | Aglassinger | |
| D541,938 S | 5/2007 | Kerr et al. | |
| D545,432 S | 6/2007 | Watanabe | |
| D547,154 S | 7/2007 | Lee | |
| D564,662 S | 3/2008 | Moses et al. | |
| D567,943 S | 4/2008 | Moses et al. | |
| D575,395 S | 8/2008 | Hushka | |
| D575,401 S | 8/2008 | Hixson et al. | |
| D582,038 S | 12/2008 | Swoyer et al. | |
| 7,517,356 B2 | 4/2009 | Heinrich | |
| 7,625,370 B2 * | 12/2009 | Hart | A61B 17/12013 606/214 |
| D617,900 S | 6/2010 | Kingsley et al. | |
| D617,901 S | 6/2010 | Unger et al. | |
| D617,902 S | 6/2010 | Twomey et al. | |
| D617,903 S | 6/2010 | Unger et al. | |
| D618,798 S | 6/2010 | Olson et al. | |
| 7,744,628 B2 | 6/2010 | Viola | |
| 7,753,909 B2 | 7/2010 | Chapman et al. | |
| D621,503 S | 8/2010 | Otten et al. | |
| D627,462 S | 11/2010 | Kingsley | |
| D628,289 S | 11/2010 | Romero | |
| D628,290 S | 11/2010 | Romero | |
| D630,324 S | 1/2011 | Reschke | |
| D649,249 S | 11/2011 | Guerra | |
| D649,643 S | 11/2011 | Allen, IV et al. | |
| D661,394 S | 6/2012 | Romero et al. | |
| 8,679,140 B2 | 3/2014 | Butcher | |
| RE44,834 E | 4/2014 | Dumbauld et al. | |
| 9,375,259 B2 | 6/2016 | Payne et al. | |
| 2005/0165444 A1 | 7/2005 | Hart et al. | |
| 2006/0111738 A1 | 5/2006 | Wenchell | |
| 2007/0118115 A1 | 5/2007 | Artale et al. | |
| 2007/0129712 A1 | 6/2007 | Neuberger | |
| 2007/0260242 A1 | 11/2007 | Dycus et al. | |
| 2010/0069903 A1 | 3/2010 | Allen, IV et al. | |
| 2010/0130971 A1 | 5/2010 | Baily | |
| 2011/0213357 A1 | 9/2011 | Schechter | |
| 2013/0245623 A1 | 9/2013 | Twomey | |
| 2013/0247343 A1 | 9/2013 | Horner et al. | |
| 2013/0253489 A1 | 9/2013 | Nau, Jr. et al. | |
| 2013/0255063 A1 | 10/2013 | Hart et al. | |
| 2013/0267948 A1 | 10/2013 | Kerr et al. | |
| 2013/0267949 A1 | 10/2013 | Kerr | |
| 2013/0274736 A1 | 10/2013 | Garrison | |
| 2013/0282010 A1 | 10/2013 | McKenna et al. | |
| 2013/0289561 A1 | 10/2013 | Waaler et al. | |
| 2013/0296848 A1 | 11/2013 | Allen, IV et al. | |
| 2013/0296854 A1 | 11/2013 | Mueller | |
| 2013/0296856 A1 | 11/2013 | Unger et al. | |
| 2013/0296922 A1 | 11/2013 | Allen, IV et al. | |
| 2013/0296923 A1 | 11/2013 | Twomey et al. | |
| 2013/0304058 A1 | 11/2013 | Kendrick | |
| 2013/0304059 A1 | 11/2013 | Allen, IV et al. | |
| 2013/0304066 A1 | 11/2013 | Kerr et al. | |
| 2013/0310832 A1 | 11/2013 | Kerr et al. | |
| 2013/0325057 A1 | 12/2013 | Larson et al. | |
| 2013/0331837 A1 | 12/2013 | Larson | |
| 2013/0338666 A1 | 12/2013 | Bucciaglia et al. | |
| 2013/0338693 A1 | 12/2013 | Kerr et al. | |
| 2013/0345701 A1 | 12/2013 | Allen, IV et al. | |
| 2013/0345706 A1 | 12/2013 | Garrison | |
| 2013/0345735 A1 | 12/2013 | Mueller | |
| 2014/0005663 A1 | 1/2014 | Heard et al. | |
| 2014/0005666 A1 | 1/2014 | Moua et al. | |
| 2014/0025052 A1 | 1/2014 | Nau, Jr. et al. | |
| 2014/0025053 A1 | 1/2014 | Nau, Jr. et al. | |
| 2014/0025059 A1 | 1/2014 | Kerr | |
| 2014/0025060 A1 | 1/2014 | Kerr | |
| 2014/0025066 A1 | 1/2014 | Kerr | |
| 2014/0025067 A1 | 1/2014 | Kerr et al. | |
| 2014/0025070 A1 | 1/2014 | Kerr et al. | |
| 2014/0025073 A1 | 1/2014 | Twomey | |
| 2014/0031821 A1 | 1/2014 | Garrison | |
| 2014/0031860 A1 | 1/2014 | Stoddard et al. | |
| 2014/0046323 A1 | 2/2014 | Payne et al. | |
| 2014/0066910 A1 | 3/2014 | Nau, Jr. | |
| 2014/0066911 A1 | 3/2014 | Nau, Jr. | |
| 2014/0074091 A1 | 3/2014 | Arya et al. | |
| 2014/0100564 A1 | 4/2014 | Garrison | |
| 2014/0100568 A1 | 4/2014 | Garrison | |

FOREIGN PATENT DOCUMENTS

| | | |
|---|---|---|
| DE | 02514501 A1 | 10/1976 |
| DE | 2627679 A1 | 1/1977 |
| DE | 03423356 A1 | 1/1986 |
| DE | 03612646 A1 | 4/1987 |
| DE | 8712328 U1 | 2/1988 |
| DE | 04303882 A1 | 8/1994 |
| DE | 04403252 A1 | 8/1995 |
| DE | 19515914 C1 | 7/1996 |
| DE | 19506363 A1 | 8/1996 |
| DE | 29616210 U1 | 11/1996 |
| DE | 19608716 C1 | 4/1997 |

(56) References Cited

FOREIGN PATENT DOCUMENTS

| | | |
|---|---|---|
| DE | 19751106 A1 | 5/1998 |
| DE | 19738457 A1 | 3/1999 |
| DE | 19751108 A1 | 5/1999 |
| DE | 19946527 C1 | 7/2001 |
| DE | 10031773 A1 | 11/2001 |
| DE | 10045375 A1 | 4/2002 |
| DE | 20121161 U1 | 4/2002 |
| DE | 102004026179 A1 | 12/2005 |
| DE | 202007009165 U1 | 8/2007 |
| DE | 202007009317 U1 | 8/2007 |
| DE | 202007009318 U1 | 8/2007 |
| DE | 202007016233 U1 | 1/2008 |
| DE | 102008018406 B3 | 7/2009 |
| EP | 1159926 A2 | 12/2001 |
| EP | 1281878 A1 | 2/2003 |
| JP | 61501068 | 9/1984 |
| JP | 6502328 | 3/1992 |
| JP | 55106 | 1/1993 |
| JP | H0540112 A | 2/1993 |
| JP | 0006030945 | 2/1994 |
| JP | 6121797 | 5/1994 |
| JP | 6285078 | 10/1994 |
| JP | 06343644 | 12/1994 |
| JP | 6511401 | 12/1994 |
| JP | 07265328 | 10/1995 |
| JP | 856955 | 5/1996 |
| JP | 08252263 | 10/1996 |
| JP | 8289895 | 11/1996 |
| JP | 8317934 | 12/1996 |
| JP | 8317936 | 12/1996 |
| JP | 910223 | 1/1997 |
| JP | 09000538 | 1/1997 |
| JP | 9122138 | 5/1997 |
| JP | 0010000195 | 1/1998 |
| JP | H1024051 A | 1/1998 |
| JP | 10155798 | 6/1998 |
| JP | H1147149 A | 2/1999 |
| JP | H1147150 A | 2/1999 |
| JP | 11070124 | 3/1999 |
| JP | 11169381 | 6/1999 |
| JP | 11192238 | 7/1999 |
| JP | 11244298 | 9/1999 |
| JP | 2000102545 A | 4/2000 |
| JP | 2000135222 A | 5/2000 |
| JP | 2000342599 A | 12/2000 |
| JP | 2000350732 A | 12/2000 |
| JP | 2001008944 A | 1/2001 |
| JP | 2001029356 A | 2/2001 |
| JP | 200103400 | 4/2001 |
| JP | 2001128990 A | 5/2001 |
| JP | 2001190564 A | 7/2001 |
| JP | 2002136525 A | 5/2002 |
| JP | 2002230072 | 8/2002 |
| JP | 2002528166 A | 9/2002 |
| JP | 2003116871 A | 4/2003 |
| JP | 2003175052 A | 6/2003 |
| JP | 2003245285 A | 9/2003 |
| JP | 2004517668 A | 6/2004 |
| JP | 2004528869 A | 9/2004 |
| JP | 2005152663 A | 6/2005 |
| JP | 2005253789 A | 9/2005 |
| JP | 2006015078 A | 1/2006 |
| JP | 2006501939 A | 1/2006 |
| JP | 2006095316 A | 4/2006 |
| JP | 2011125195 A | 6/2011 |
| SU | 401367 A1 | 10/1973 |
| WO | 0036986 A1 | 6/2000 |
| WO | 0059392 A1 | 10/2000 |
| WO | 0115614 A1 | 3/2001 |
| WO | 0154604 A1 | 8/2001 |
| WO | 0245589 A2 | 6/2002 |
| WO | 2006021269 A1 | 3/2006 |
| WO | 05110264 A3 | 4/2006 |
| WO | 2008040483 A1 | 4/2008 |
| WO | 2011018154 A1 | 2/2011 |

OTHER PUBLICATIONS

U.S. Appl. No. 09/177,950, filed Oct. 23, 1998, Randel A. Frazier.
U.S. Appl. No. 09/387,883, filed Sep. 1, 1999, Schmaltz et al.
U.S. Appl. No. 09/591,328, filed Jun. 9, 2000, Ryan et al.
U.S. Appl. No. 12/336,970, filed Dec. 17, 2008, Sremcich et al.
U.S. Appl. No. 13/731,674, filed Dec. 31, 2012, Siebrecht.
Michael Choti, "Abdominoperineal Resection with the LigaSure Vessel Sealing System and LigaSure Atlas 20 cm Open Instrument"; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps", Feb. 6, 1967 (Feb. 6, 1965), British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte,NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.

(56) References Cited

OTHER PUBLICATIONS

Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J. Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrell et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" Miccai 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.

\* cited by examiner

ELECTROSURGICAL INSTRUMENT INCLUDING AN ADHESIVE APPLICATOR ASSEMBLY

CROSS-REFERENCE TO RELATED APPLICATIONS

This application is a continuation of U.S. patent application Ser. No. 14/054,173, filed on Oct. 15, 2013, which claims priority to and the benefit of U.S. Provisional Patent Application Ser. No. 61/718,067, filed on Oct. 24, 2012, the entire contents of each of which are hereby incorporated by reference.

BACKGROUND

Technical Field

The present disclosure relates to an electrosurgical instrument and, more particularly, to an adhesive applicator assembly configured for use with the electrosurgical instrument.

Description of Related Art

Electrosurgical forceps are well known in the medical arts. For example, electrosurgical endoscopic forceps are utilized in surgical procedures, e.g., laparoscopic surgical procedure, where access to tissue is accomplished through a cannula or other suitable device positioned in an opening on a patient. The endoscopic forceps, typically, include a housing, a handle assembly including a movable handle, a drive assembly, a shaft and an end effector assembly attached to a distal end of the shaft. Typically, the endoscopic forceps utilize both mechanical clamping action and electrical energy to effect hemostasis by heating the tissue and blood vessels to coagulate, cauterize, seal, cut, desiccate, and/or fulgurate tissue. In particular, the jaw members operably communicate with the drive assembly to manipulate tissue, e.g., grasp and seal tissue, and the jaw members have respective seal plates secured to the jaw housing of the respective jaw members to seal tissue.

In order to effect proper hemostatic fusion of vessels or tissue, two predominant mechanical parameters should be accurately controlled: the pressure applied to the vessels or tissue; and the minimum distance or "gap" between the electrodes of the jaw members. As can be appreciated, both of these parameters may be affected by the thickness of the vessels or tissue being treated. Experience in vessel sealing, for example, has shown that accurate control of pressure is important for achieving reliable formation of hemostatic seals. Too little pressure may result in poor adhesion giving seals that are likely to open or leak. Too much pressure may damage or displace tissue structures essential for the formation of strong seals. Accurate control of the gap between electrodes is important to prevent short circuit conditions and to ensure that thin tissue structures can be reliably fused. Electrode gaps of between about 0.001 inches to about 0.006 inches have proven to be effective on a variety of tissue conditions; however, it may be beneficial to adjust this range for specific situations.

To achieve proper results, the above-described parameters should be controlled, which can be difficult and time consuming.

SUMMARY

In view of the foregoing, there exists a need for improved end effector assemblies that can effectively improve the seal quality.

In accordance with an embodiment of the present disclosure, there is provided an electrosurgical instrument for sealing and/or cutting tissue. The surgical instrument includes a handle assembly and an end effector assembly operatively connected to the handle assembly. In particular, the end effector assembly includes a first jaw member including a first jaw housing and a first electrically conductive surface defining a plurality of bores, a second jaw member including a second jaw housing and a second electrically conductive surface, and an adhesive applicator assembly disposed in the first jaw member. At least one of the first and second jaw members is movable relative to the other between a first position in which the first and second jaw members are disposed in spaced apart relation relative to one another and a second position in which the first and second jaw members cooperate to grasp tissue therebetween. The first and second electrically conductive surfaces are configured to effect a tissue seal. The adhesive applicator assembly includes a first platform defining a first reservoir therein and a plurality of first needles in communication with the first reservoir. The first platform is movable between a neutral position in which the plurality of first needles are disposed within the first jaw housing and an actuated position in which the plurality of first needles extend through the respective plurality of bores defined in the first electrically conductive surface.

In an embodiment, the electrosurgical instrument may further include a liquid adhesive source in fluid communication with the first reservoir defined in the first platform. In another embodiment, the second electrically conductive surface may define a plurality of recesses configured to at least partially receive respective first needles therein. In yet another embodiment, each first needle may define plurality of apertures in communication with the first reservoir in the platform. In addition, the first platform may be coupled to a first biasing member to bias the first platform toward the neutral position.

In still another embodiment, the end effector assembly may further include a first actuation assembly including a first wedge and a first actuation rod coupled to the first wedge for concomitant translation therewith. Translation of first actuation rod may cause transition of the first platform between the neutral and actuated positions.

In still yet another embodiment, the end effector assembly may further include a second adhesive applicator assembly disposed in the second jaw member. In particular, the second adhesive applicator assembly may include a second platform defining a second reservoir therein and a plurality of second needles in communication with the second reservoir. The second platform may be movable between a first state in which the plurality of second needles are disposed within the second jaw housing and a second state in which the plurality of second needles extend through respective plurality of second bores defined in the second electrically conductive surface. The plurality of second needles may each define a plurality of apertures in communication with the second reservoir. One of the plurality of apertures may be defined at a tip portion of the respective second needles. In an embodiment, the one of the plurality of apertures defined at the tip portion of the respective second needles may be configured to receive the respective first needle therethrough.

In still yet another embodiment, the second adhesive applicator assembly may further include a second biasing member to bias the second platform toward the first state. The first and second needles may be spaced apart when the first needles are in the actuated position and the second needles are in the second state.

In certain embodiments, the second applicator assembly may further include a second wedge and a second actuation rod coupled to the second wedge for concomitant translation therewith. In particular, translation of second actuation rod may cause transition of the second platform between the first and second states. In an embodiment, at least one of the electrically conductive surfaces may define a channel extending along a length thereof. The channel may be configured for reciprocation of a knife member therein. The liquid adhesive source includes a time or heat-activated adhesive fluid.

In accordance with another aspect of the present disclosure, there is provided a method of sealing tissue using an electrosurgical instrument. The method includes grasping tissue between the pair of jaw members having electrically conductive surfaces, energizing the electrically conductive surfaces with electrosurgical energy to seal tissue, and supplying an adhesive to tissue through channels formed in a plurality of needles disposed on at least one jaw member and in fluid communication with a supply of adhesive.

In still another embodiment, the step of supplying adhesive may include passing the adhesive through a plurality of apertures formed in each of the plurality of needles.

In still yet another embodiment, supplying an adhesive to tissue may include supplying the adhesive to a first surface of tissue opposing the first jaw member and a second surface of tissue opposing the second jaw member.

In another embodiment, the adhesive may be a time or heat-activated adhesive.

BRIEF DESCRIPTION OF THE DRAWINGS

Various embodiments of the present disclosure are described hereinbelow with references to the drawings, wherein.

DETAILED DESCRIPTION

Figure 1:
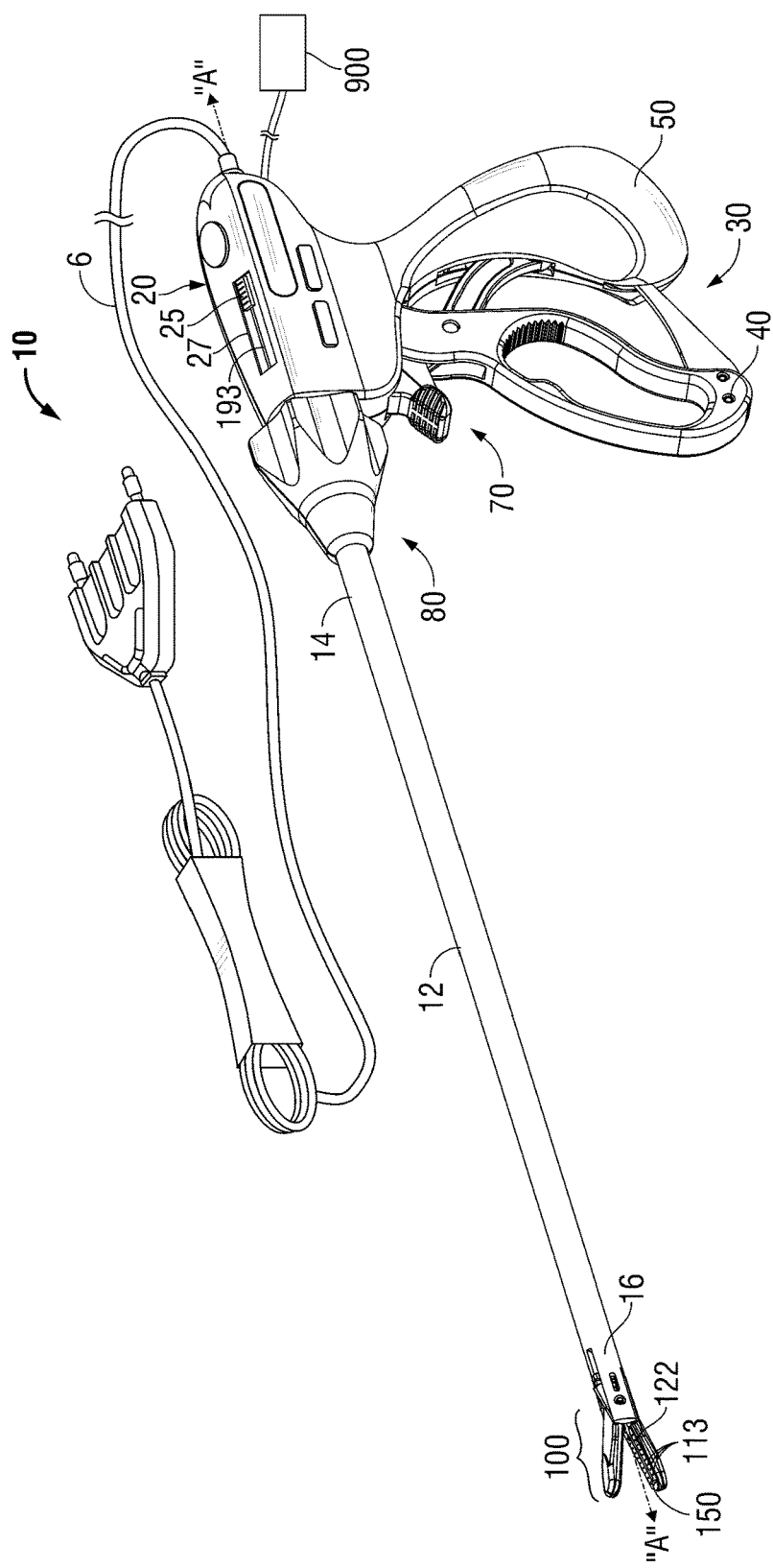
FIG. 1 is a perspective view of an endoscopic electrosurgical instrument including an adhesive applicator assembly in accordance with an illustrative embodiment of the present disclosure.

Embodiments of the present disclosure are described in detail with reference to the drawings, in which like reference numerals designate identical or corresponding elements in each of the several views. As used herein, the term "distal," as is conventional, will refer to that portion of the instrument, apparatus, device or component thereof which is farther from the user while, the term "proximal," will refer to that portion of the instrument, apparatus, device or component thereof which is closer to the user. In the following description, well-known functions or constructions are not described in detail to avoid obscuring the present disclosure in unnecessary detail.

With reference to FIG. 1, there is illustrated an endoscopic electrosurgical instrument 10 in accordance with an embodiment of the present disclosure. Instrument 10 includes an elongated body 12 with a proximal portion 14 and a distal portion 16. Elongated body 12 extends distally from a handle assembly 30 and defining a longitudinal axis "A-A." An end effector assembly 100 is coupled to distal portion 16 of elongated body 12 and includes opposing jaw members 110, 120 (FIG. 2) that mutually cooperate to grasp, seal and divide tubular vessels and vascular tissue, as will be described in detail below. Instrument 10 also includes electrosurgical cable 6 that connects instrument 10 to a generator (not shown) or other suitable energy source. Alternatively, instrument 10 may be configured as a battery-powered instrument to facilitate an untethered operation. Cable 6 includes one or more wires (not shown) having sufficient length to extend through elongated body 12 in order to provide electrical energy to at least one of jaw members 110, 120 of end effector assembly 100.

With continued reference to FIG. 1, handle assembly 30 includes a housing 20, a switch assembly 70, and a rotating assembly 80 configured to rotate with respect to housing 20 to selectively position end effector assembly 100 to any rotational orientation about longitudinal axis "A-A." Handle assembly 30 further includes a fixed handle 50 and a movable handle 40. Fixed handle 50 is integrally associated with housing 20 and movable handle 40 is movable relative to fixed handle 50 to actuate the opposing jaw members 110, 120 (FIG. 2) of end effector assembly 100. In particular, movable handle 40 imparts movement of jaw members 110, 120 about a pivot 160 (FIG. 2) from an open position in which jaw members 110, 120 are disposed in a spaced apart relation relative to one another to a clamping or closed position in which jaw members 110, 120 cooperate to grasp tissue therebetween.

Elongated body 12 has a proximal end 14 that mechanically engages housing 20. In particular, proximal end 14 of elongated body 12 mechanically engages rotating assembly 80 to facilitate rotation of end effector assembly 100 to any rotational orientation about longitudinal axis "A-A." Details relating to the mechanically cooperating components of elongated body 12 and rotating assembly 80 are described in commonly owned U.S. Patent Application Publication No. 2007/0260242 entitled "Vessel Sealer and Divider."

Figure 2:
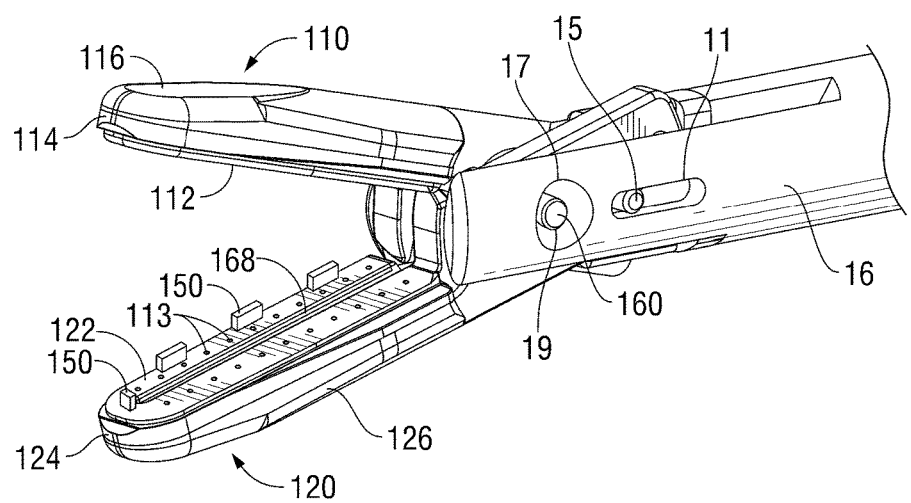
FIG. 2 is an enlarged partial, perspective view of the distal end of the instrument of FIG. 1 illustrating jaw members of an end effector in an open, spaced apart configuration.
Figure 3:
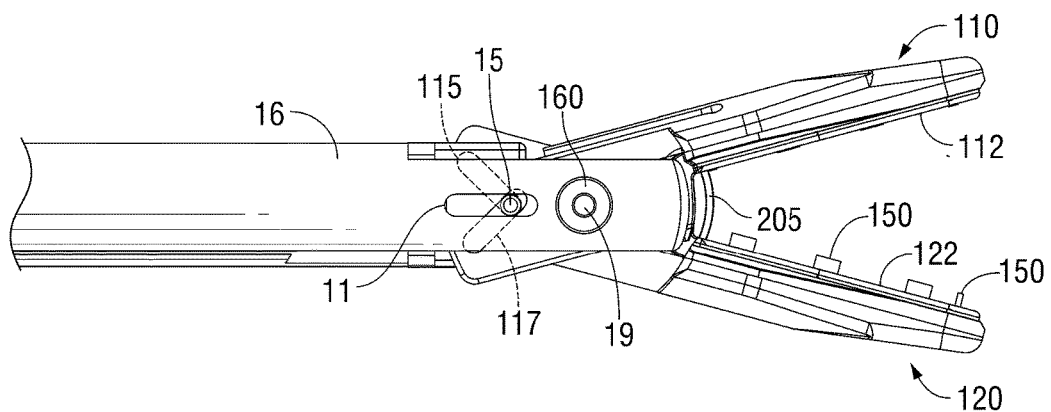
FIG. 3 is a partial, side view of the instrument of FIG. 2.

With reference to FIGS. 2 and 3, elongated body 12 may include one or more known mechanically engaging components that are designed to securely receive and engage end effector assembly 100 such that jaw members 110, 120 are pivotable relative to one another to engage and grasp tissue therebetween. In the illustrated embodiment, distal end portion 16 of elongated body 12 defines a pair of camming slots 11 on lateral sides thereof (only one shown) configured to slidably receive a camming pin 15 therein. In addition, distal end portion 16 of elongated body 12 further defines a pivot bore 17 configured to receive a pivot pin 19 to pivotally couple jaw members 110, 120 about pivot 160. Jaw members 110, 120 define camming slots 115, 117 (shown in phantom in FIG. 3), respectively. Camming slots 115, 117 are configured to slidably receive camming pin 15 therein. Each camming slot 115, 117 defines an acute angle with respect to longitudinal axis "A-A" (FIG. 1), whereby sliding movement of camming pin 15 within camming slots 11, 115, 117 pivotally moves jaw members 110, 120 between the open or spaced apart position and the closed or clamping position about pivot 160.

With continued reference to FIGS. 2 and 3, jaw members 110, 120 are generally symmetrical and include similar component features, which cooperate to permit facile rotation about pivot 160 to effect sealing and dividing of tissue. Jaw member 110 includes a jaw housing 116 coated with an insulative coating 114 to reduce stray current concentrations during sealing and an electrically conductive sealing surface 112. However, in some embodiments, jaw housing 116 may include an insulative substrate or insulator configured to securely engage electrically conductive sealing surface 112. This may be accomplished by stamping, by overmolding, by overmolding a stamped electrically conductive sealing plate and/or by overmolding a metal injection molded seal plate. All of these manufacturing techniques produce an electrode having an electrically conductive sealing surface that is substantially surrounded by an insulating substrate. In certain instances, it may prove advantageous to provide an exterior portion of jaw housing 116 that is made from metal and an interior portion (e.g., a portion that is configured to support a seal plate thereon) of jaw housing 116 that is made from plastic. In this instance, the interior portion serves as an insulative barrier between the seal plate and the exterior portion of jaw housing.

Similarly, jaw member 120 includes a jaw housing 126 coated with an insulative coating 124 to reduce stray current concentrations during sealing and an electrically conductive sealing surface 122. However, in some embodiments, jaw housing 126 may include an insulator and an electrically conductive sealing surface that is dimensioned to securely engage insulator. Electrically conductive sealing surface 122 defines a longitudinally oriented channel 168 configured to receive a knife blade 205 therethrough. Channel 168 facilitates longitudinal reciprocation of knife blade 205 along a preferred cutting plane to effectively and accurately separate tissue along the formed tissue seal. Although not shown, jaw member 110 may also define a knife channel that cooperates with channel 168 to facilitate translation of knife blade 205 through tissue.

Jaw members 110, 120 are electrically isolated from one another such that electrosurgical energy can be effectively transferred through tissue to form a tissue seal. Electrically conductive sealing surfaces 112, 122 are also isolated from the remaining operative components of end effector assembly 100 and elongated body 12. A plurality of stop members 150 are employed to regulate the gap distance between sealing surfaces 112, 122 to insure accurate, consistent and reliable tissue seals. In one embodiment, gap distances within the range of about 0.001 inches to about 0.006 inches are known to produce quality seals.

Figure 4:
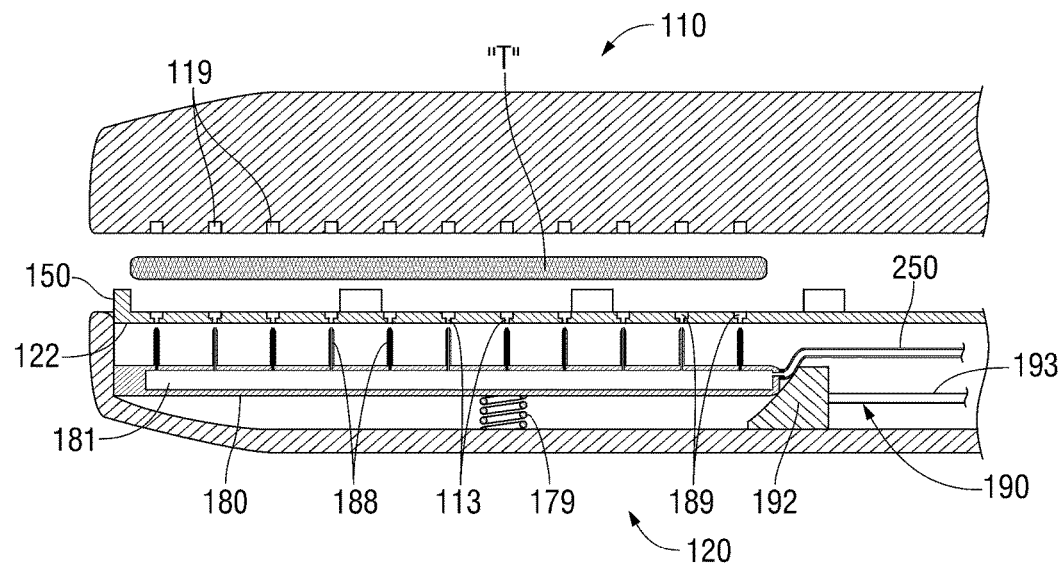
FIG. 4 is a partial, longitudinal cross-sectional view of the end effector of the instrument of FIG. 2 illustrating a platform of the adhesive applicator assembly in a neutral state.
Figure 5:
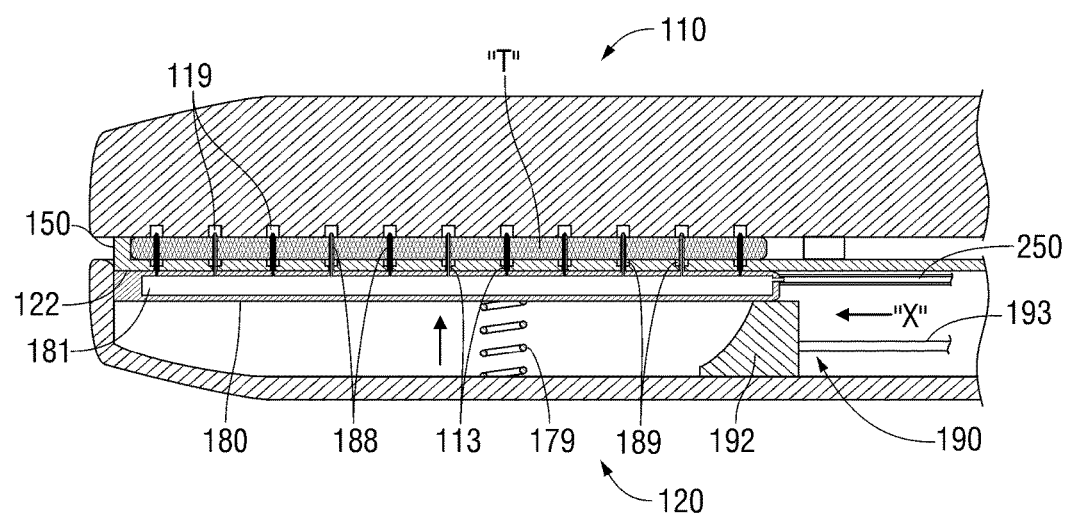
FIG. 5 is a partial, longitudinal cross-sectional view of the end effector of FIG. 4 illustrating the platform in an actuated state.

With reference now to FIGS. 4 and 5, jaw member 120 includes a platform 180 including a plurality of needles 188 extending from platform 180 and directed transversely towards jaw member 110. Platform 180 defines a reservoir 181 in fluid communication with an interior fluid passageway or channel 187 formed in each needle 188 (FIG. 6) and with a liquid adhesive supply 900 (FIG. 1) having liquid adhesive maintained under pressure via a conduit 250 extending through jaw member 120. Alternatively, a predetermined amount of liquid adhesive may be disposed in conduit 250 and/or reservoir 181 to facilitate untethered operation. In particular, conduit 250 may include a plunger (not shown) operatively coupled with a sliding member 25 in housing 20. Sliding member 25 is movable within a slot 27 defined in housing 20, whereby translation of sliding member 25 actuates the plunger to move the liquid adhesive in conduit 250 and/or reservoir 181 through each channel 187 formed in respective needle 188.

Sealing surface 122 defines a plurality of bores 113 configured to slidably receive respective needles 188 therethrough. Platform 180 is movable between an actuated state (FIG. 5) in which the plurality of needles 188 extend through a plurality of corresponding bores 113 formed in sealing surface 122 and a neutral state (FIG. 4) in which the plurality of needles 188 are spaced apart from bores 113. In one embodiment, platform 180 is coupled to a biasing member such as spring 179 to bias platform 180 toward the neutral state. Jaw member 120 further includes an actuation assembly 190 to actuate platform 180 between the actuated and neutral states. In particular, actuation assembly 190 includes an actuation wedge 192 and an actuation rod 193 operatively coupled to actuation wedge 192 to enable translation along longitudinal axis "A-A" as a single construct with actuation wedge 192. Actuation rod 193 is operatively coupled with sliding member 25 (FIG. 1) in housing 20. Translation of sliding member 25 within slot 27 causes a concomitant translation of actuation wedge 192, which in turn moves platform 180 between the neutral and actuated states. In an embodiment, sliding member 25 is coupled with the plunger and actuation wedge 192 such that a distal translation of sliding member 25 causes concomitant translation of actuation wedge 192 which moves platform 180 from the neutral state to the actuated state. In particular, translation of sliding member 25 to the distal-most position in slot 27 causes the plunger to move the liquid adhesive through channel 187 defined in respective needles 188. Actuation rod 193 is relatively flexible to accommodate pivotal movement of jaw members 110, 120. Jaw member 110 defines a plurality of recesses 119 formed in the interior surface of jaw member 110 in alignment with the respective needles 188 and being configured to receive respective tip of needles 188.

With particular reference to FIG. 5, when actuation rod 193 is translated distally in the direction of an arrow "X," a camming surface 192a formed on actuation wedge 192 contacts platform 180. The distal movement of actuation wedge 192 and the resulting camming action of camming surface 192a on platform 180 causes platform 180 to move toward jaw member 110 in the direction of an arrow "Y"

toward the actuated state position. In this manner, needles 188 extend through the respective bores 113 formed in sealing surface 122 and tissue "T." The tip portion of respective needles 188 is disposed in respective recesses 119. At this time, liquid adhesive may be supplied to the plurality of needles 188 through conduit 250, as will be described in detail hereinbelow.

Figure 6:
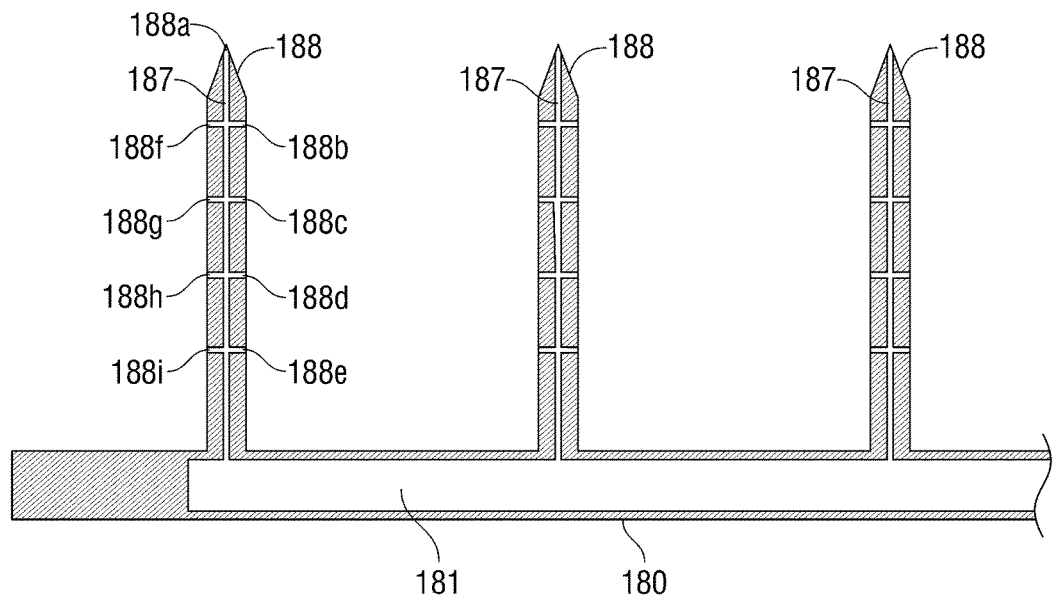
FIG. 6 is a partial, enlarged cross-sectional view of needles of the adhesive applicator assembly of FIG. 4.
Figure 8:
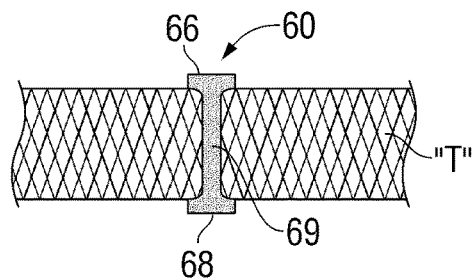
FIG. 8 is a cross-sectional view of an adhesive structure formed in tissue of FIG. 5.

With reference now to FIG. 6, each needle 188 defines a channel 187 in fluid communication with a plurality of apertures 188a-188i defined in various points on needle 188. Under such a configuration, when liquid adhesive is supplied to the plurality of needles 188 in the actuation position, the adhesive supplied through channel 187 in each needle 188 is released through the plurality of apertures 188a-188i. Due to the positioning of apertures 188a-188i along the length of needles 188, the liquid adhesive may be applied to both the top and bottom surfaces of tissue "T," as well as the inside of tissue "T." In this manner, the liquid adhesive cures to form a plurality of rivet-like adhesive structures 60, as best shown in FIG. 8. In particular, adhesive structures 60 include a top surface 66 in a superposed relation with a top surface of tissue (i.e., tissue surface opposing sealing surface 112 of jaw member 110) and a bottom surface 68 in a superposed relation with a bottom surface of tissue (i.e., tissue surface opposing sealing surface 122 of jaw member 120). Additionally, adhesive structures 60 include a connecting web or stem portion 69 inter-connecting top and bottom surfaces 66, 68 and extending through tissue "T."

Figure 7:
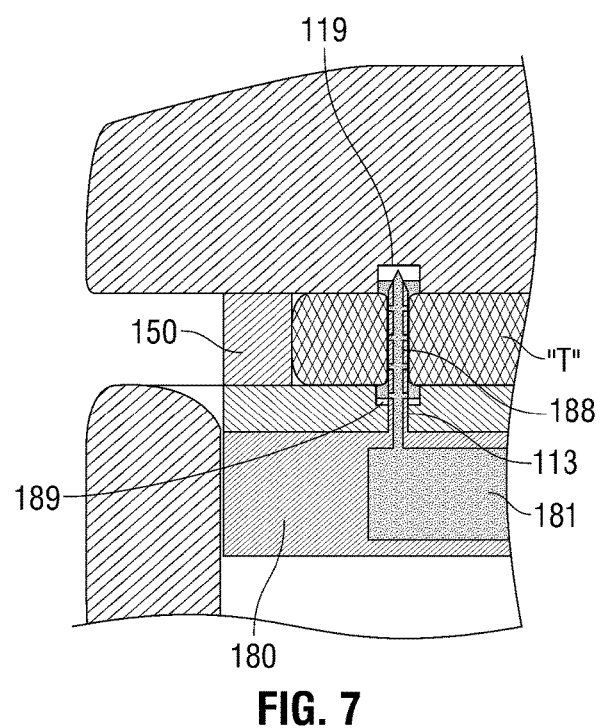
FIG. 7 is a partial, enlarged cross-sectional view of the end effector of FIG. 5.

With reference now to FIG. 7, platform 180 includes a plurality of recesses 189 formed adjacent respective bores 113. Recesses 189 are configured to receive needles 188 therethrough, such that when the liquid adhesive is supplied through needle 188, recesses 189 facilitate formation of bottom surface 68 (FIG. 8) of each adhesive structure 60.

In use, after clamping the tissue between opposing jaw members 110 and 120 by actuating movable handle 40 (FIG. 1), the user energizes the opposing electrically conductive sealing surfaces 112, 122 to effectively seal tissue "T" disposed between jaw members 110, 120. Once tissue "T" is sealed or otherwise treated, actuation assembly 190 may be actuated through actuation of sliding member 25 to place the plurality of needles in the actuated state in which the plurality of needles 188 penetrate through tissue "T" and at least partially engage recesses 119 defined in sealing surface 112 of jaw housing 116. The liquid adhesive maintained under pressure in liquid adhesive supply 900 may be supplied to the plurality of needles 188 through conduit 250. The liquid adhesive travels through each of the plurality of apertures 188a-188i in various points in each of needle 188 and forms adhesive structure 60 as shown in FIG. 8. The rivet-like adhesive structure 60 improves the seal quality of tissue "T," by reducing, for example, stress-concentration points on tissue "T."

Figure 9:
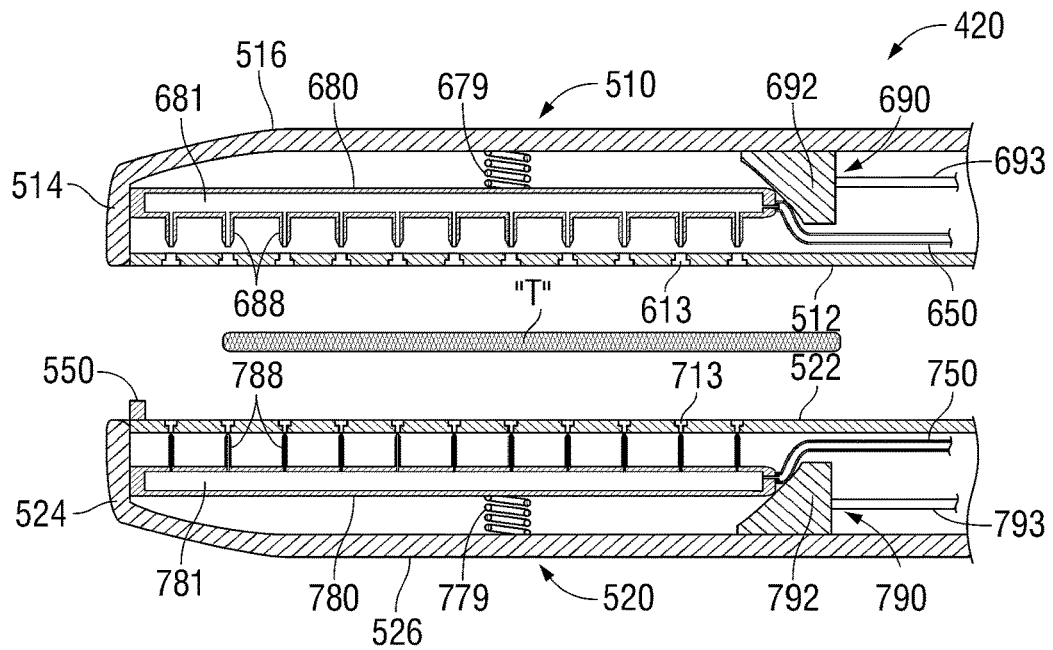
FIG. 9 is a partial, longitudinal cross-sectional view of an end effector for use with the instrument of FIG. 1 in accordance with another illustrative embodiment of the present disclosure which shows platforms of an adhesive applicator in a neutral state.
Figure 10:
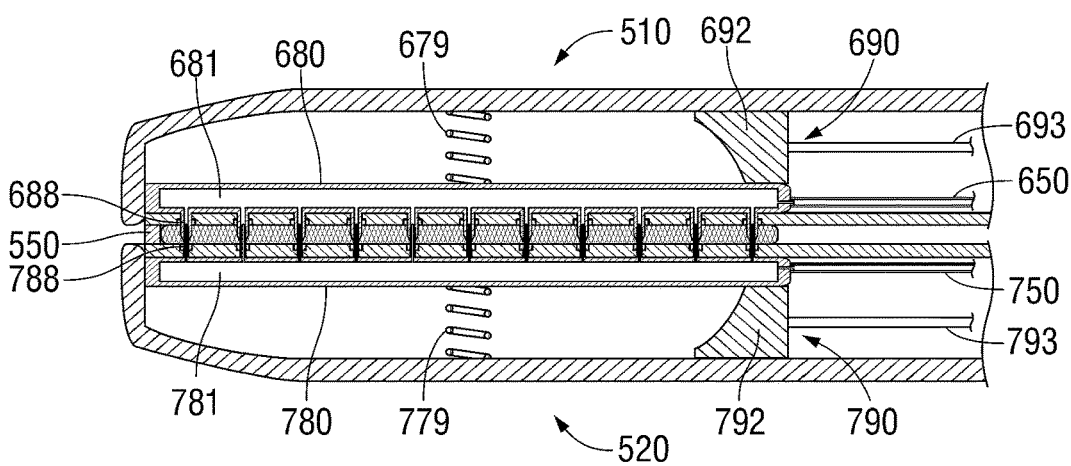
FIG. 10 is a partial, longitudinal cross-sectional view of the end effector of FIG. 9 illustrating platforms of adhesive applicator assemblies in an actuated state.

With reference now to FIGS. 9 and 10, an end effector assembly 420 in accordance with another embodiment of the present disclosure is shown. End effector assembly 420 includes pivotally associated jaw members 510, 520. The basic structure of jaw members 510, 520 are substantially the same as those of jaw members 110, 120, and thus will not be described in detail herein.

Jaw member 510 includes a jaw housing 516 coated with an insulative coating 514 to reduce stray current concentrations during sealing and an electrically conductive sealing surface 512. In contrast to end effector assembly 100 described hereinabove, jaw member 510 includes a plurality of needles 688 on a platform 680 that is movable between a neutral state in which the plurality of needles 688 are spaced apart from the plurality of bores 613 defined in conductive sealing surface 512 corresponding to the plurality of needles 688 and an actuated state in which the plurality of needles 688 extend through the plurality of corresponding bores 613, as shown in FIG. 10. Platform 680 defines a reservoir 681 in fluid communication with each needle 688. Reservoir 681 is in fluid communication with liquid adhesive supply 900 (FIG. 1) via a conduit 650 extending through jaw member 510. Platform 680 is coupled to a biasing member such as a spring 679 to bias platform 680 toward the neutral state. Jaw member 510 further includes an actuation assembly 690 to actuate platform 680 between the actuated and neutral states. In particular, actuation assembly 690 includes an actuation wedge 692 and an actuation rod 693 operatively coupled to actuation wedge 692 to enable a unitary translation with actuation wedge 692. Actuation assembly 690 may be operatively coupled to sliding member 25 of housing 20. The operation of actuation assembly 690 through sliding member 25 is substantially the same as that of actuation assembly 190, and thus will not be described herein. In addition, actuation rod 693 is relatively flexible to accommodate pivotal movement of jaw members 510, 620.

With continued reference to FIG. 9, jaw member 520 is substantially the same as jaw member 120 described hereinabove. Jaw member 520 includes a jaw housing 526 coated with an insulative coating 524 to reduce stray current concentrations during sealing and an electrically conductive sealing surface 522. A plurality of stop members 550 may be employed to regulate the gap distance between sealing surfaces 512, 522 to insure accurate, consistent and reliable tissue seals. Jaw member 520 includes a platform 780 including a plurality of needles 788. Platform 780 defines a reservoir 781 in fluid communication with each needle 788. Reservoir 781 is also in fluid communication with liquid adhesive supply 900 having liquid adhesive maintained under pressure via a conduit 750 extending through jaw member 520. Sealing surface 522 defines a plurality of bores 713 configured to slidably receive respective needles 788 therethrough. Platform 780 is movable between an actuated state (FIG. 10) in which the plurality of needles 788 extend through bores 713 defined in sealing surface 522 and a neutral state in which the plurality of needles 188 are spaced apart from bores 713. In particular, platform 780 is coupled to a biasing member such as a spring 779 to bias platform 780 toward the neutral state. Jaw member 520 further includes an actuation assembly 790 to actuate platform 780 between the actuated and neutral states, as described with jaw member 510 hereinabove. In particular, actuation assembly 790 includes an actuation wedge 792 and an actuation rod 793 operatively coupled to actuation wedge 792. In particular, actuation rod 793 is relatively flexible to accommodate pivotal movement of jaw members 510, 520.

Figure 11:
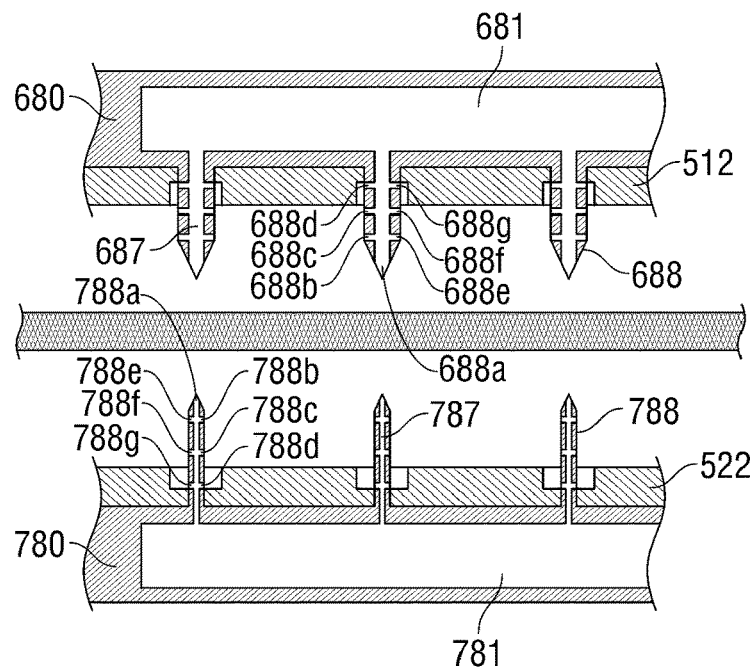
FIG. 11 is a partial, enlarged longitudinal cross-sectional view of the platforms of FIG. 9 in the neutral state.
Figure 12:
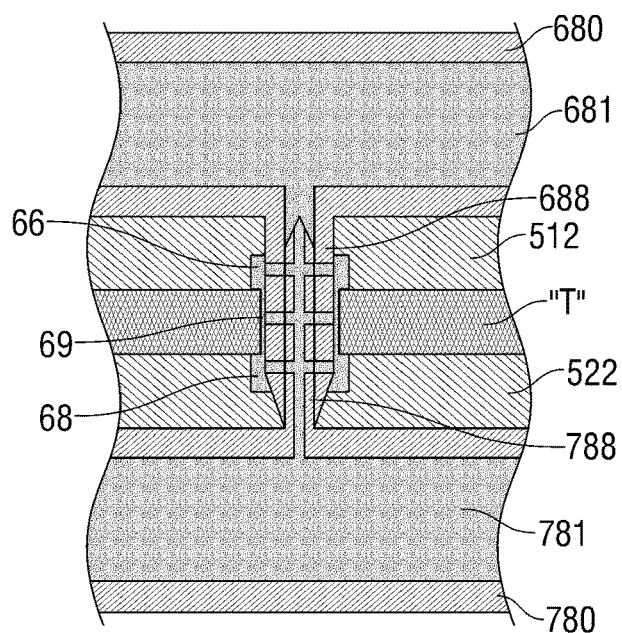
FIG. 12 is a partial, enlarged longitudinal cross-sectional view of the platforms of FIG. 10 in the actuated state.

With reference now to FIGS. 10-12, needles 688 disposed in jaw member 510 have channels 687 formed longitudinally therein with diameters that are sufficiently larger than the outer diameter of needles 788 of jaw member 520, whereby when both platforms 680, 780 are actuated toward each other, needles 788 are slidably received within the channels 687 of respective needles 688 in vertical registration. Needles 688, 788 may be actuated simultaneously or in sequence. When needles 688 are simultaneously actuated with needles 788, needles 788 each having a smaller diameter than that of needles 688 are received within the channels 687 of respective needles 688. Channels 687 are formed to be in fluid communication with a plurality of apertures 688a-688g defined in various points on needle 688. Aperture 688a of needle 688 is configured to receive respective needle 788 into channel 687. Similarly, needle 788 defines a channel 787 in communication with a plurality of apertures 788a-788g defined in various points on needle 788. Apertures 688a-688g are aligned with apertures 788a-788g, when needles 788 are disposed in respective needles 688. In this manner, when liquid adhesive is supplied through either of channels 687, 787 of needles 688, 788, adhesive forms adhesive structure 60 including top and bottom surfaces 66, 68, as well as stem portion 69 inter-connecting top and bottom surfaces 66, 68 through tissue "T."

Figure 13:
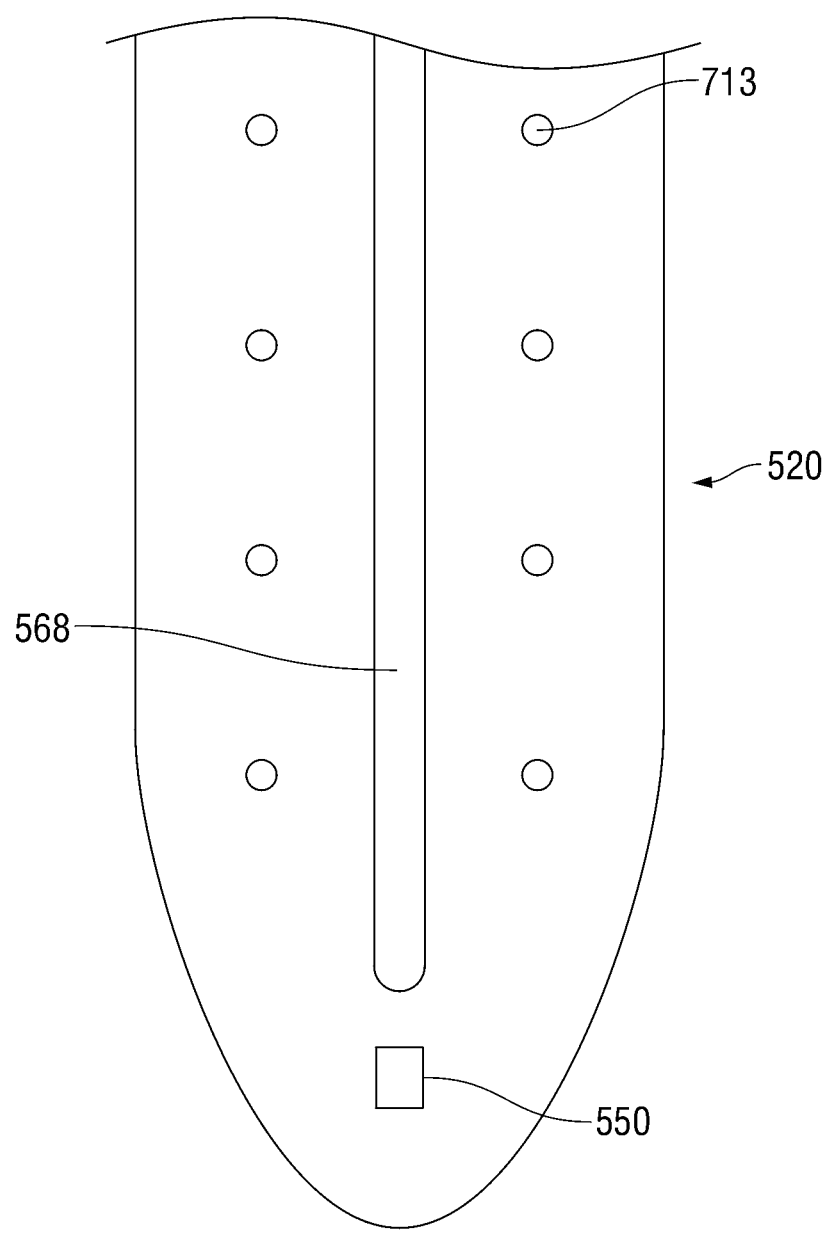
FIG. 13 is a partial, top view of a jaw member of the end effector of FIG. 9.

Alternatively, it is contemplated that needles 688 may be utilized to merely pierce through tissue "T" to establish an enlarged opening/bore through tissue "T" to facilitate insertion of needle 788 and formation of adhesive structure 60 in tissue "T." Accordingly, under such a configuration, only needles 788 need to be connected to the adhesive supply (not shown) to supply liquid adhesive to needles 788 through conduit 750. As shown in FIG. 13, bores 713 are symmetrically arranged with respect to knife channel 568. However, bores 713 may be arranged to meet the needs of the particular surgical procedure being performed.

Figure 14:
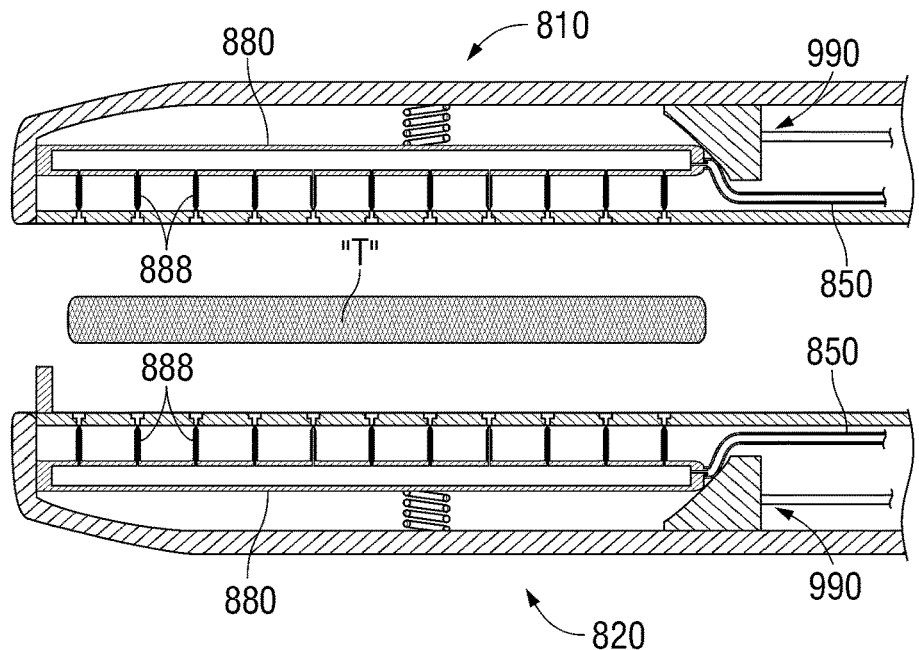
FIG. 14 is a partial, longitudinal cross-sectional view of an end effector for use with the instrument of FIG. 1 in accordance with still another embodiment of the present disclosure, which shows platforms of adhesive applicator assemblies in a neutral state.
Figure 15:
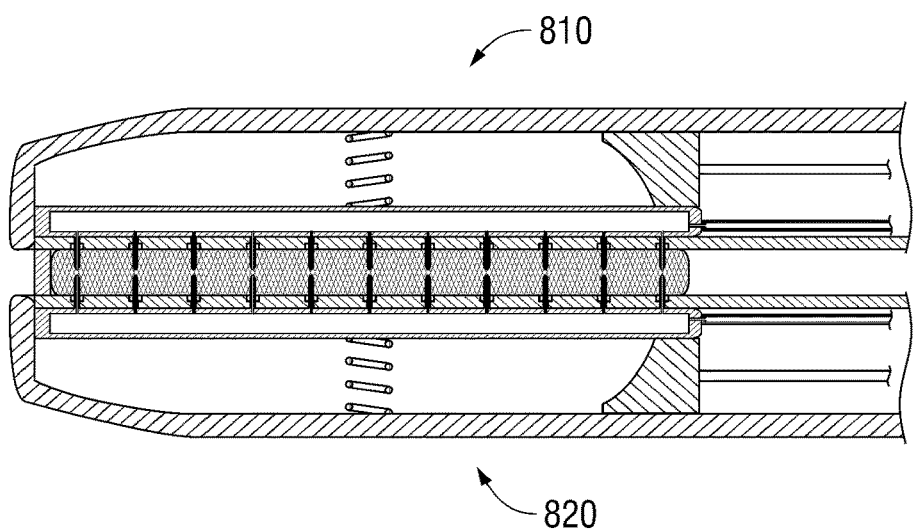
FIG. 15 is a partial, longitudinal cross-sectional view of the end effector of FIG. 14 illustrating platforms of adhesive applicator assemblies in an actuated state.
Figure 16:
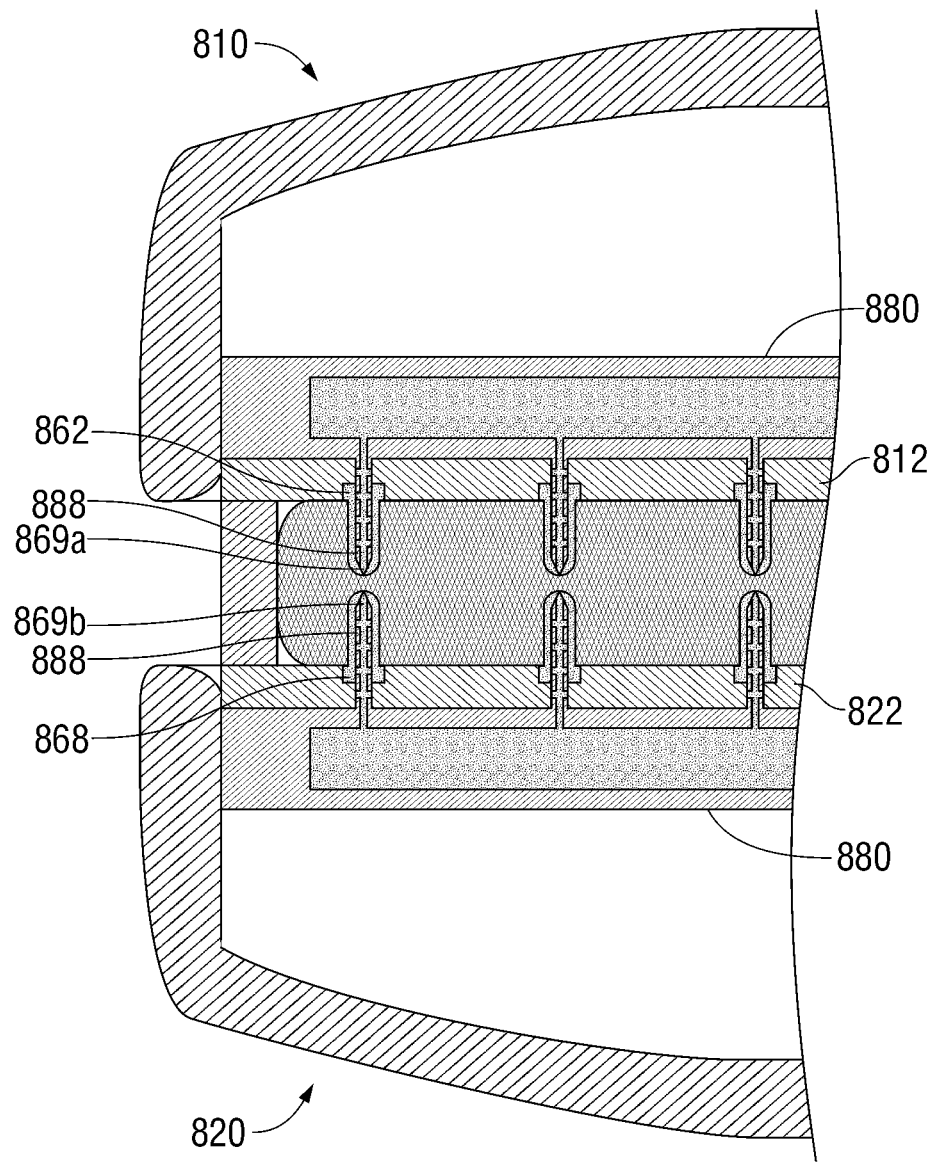
FIG. 16 is a partial, enlarged longitudinal cross-sectional view of the end effector of FIG. 15.

With reference now to FIGS. 14-16, it is further contemplated that a plurality of substantially identical needles 888 may be utilized in both jaw members 810, 820. Needles 888 and platforms 880, as well as an actuation assembly 990 in jaw members 810, 820 are substantially identical to those of jaw member 120, and thus will not be described herein.

However, in contrast to end effectors 100, 400 described hereinabove, needles 888 are configured to only partially penetrate through tissue "T." In this manner, needles 888 disposed in jaw member 810 provide the liquid adhesive that forms a top surface 862 and a stem portion 869a, and needles 888 disposed in jaw member 820 supply the liquid adhesive to form a bottom surface 868, as well as stem portion 869b. Under such a configuration, two distinctive and independent adhesive structures 860 including stem portions 869a, 869b are formed which may further reduce stress concentrations on tissue "T."

It is further contemplated that the liquid adhesive may be a time or heat-activated adhesive or a heat-enhanced adhesive to facilitate and/or to expedite the formation of the adhesive structure.

While several embodiments of the disclosure have been shown in the drawings, it is not intended that the disclosure be limited thereto, as it is intended that the disclosure be as broad in scope as the art will allow and that the specification be read likewise. For example, in certain instances, it may prove advantageous to utilize an electrode instead of a knife blade 205 to sever tissue. In addition, while rivet-like adhesive structure 60 has been described to form after forming the seal, adhesive structure 60 may be formed prior to the formation of the seal. In addition, rivet-like adhesive structures 60 may be selectively formed in tissue "T," based upon stress concentration in tissue detected through a use of sensors. In addition, while the illustrative embodiments have been shown with endoscopic instruments, the embodiments of the present disclosure may be used in open surgery instruments. Therefore, the above description should not be construed as limiting, but merely as exemplifications of particular embodiments. Those skilled in the art will envision other modifications within the scope and spirit of the claims appended hereto.

What is claimed is:

1. An electrosurgical instrument for sealing and/or cutting tissue, comprising:
an end effector assembly including:
 a first jaw member including a first electrically conductive surface having a plurality of bores defined therein;
 a second jaw member including a second electrically conductive surface, at least one of the first or second jaw members movable relative to the other to grasp tissue therebetween; and
an adhesive applicator assembly including a plurality of first needles operatively mounted in the first jaw member, a plurality of second needles operatively mounted in the second jaw member, and a platform defining an adhesive reservoir in fluid communication with the plurality of first needles and an adhesive fluid source, at least one of the plurality of first or second needles is movable relative to the first or second electrically conductive surfaces, the plurality of first needles dimensioned to be received in the corresponding plurality of second needles when the first and second jaw members are aligned.

2. The surgical instrument according to claim 1, wherein at least one needle of the plurality of first or second needles defines a plurality of apertures in communication with the adhesive reservoir of the platform.

3. The surgical instrument according to claim 1, wherein the at least one needle of the plurality of first or second needles defines apertures such that the adhesive fluid creates a rivet-like structure on tissue.

4. The surgical instrument according to claim 1, wherein the end effector assembly further includes an actuation assembly including a wedge and an actuation rod coupled to the wedge for concomitant translation therewith, translation of the actuation rod causing transition of the platform between a neutral position and an actuated position in which the plurality of first or second needles extends through the first or second electrically conductive surface.

5. The surgical instrument according to claim 4, wherein the platform is coupled to a biasing member to bias the platform toward the neutral position.

6. The surgical instrument according to claim 1, wherein the second electrically conductive surface defines a plurality of recesses in registration with the plurality of bores of the first electrically conductive surface when tissue is grasped between the first and second jaw members.

7. The surgical instrument according to claim 1, wherein at least one of the first or second electrically conductive surfaces defines a channel extending along a length thereof, the channel configured for reciprocation of a knife blade therein.

8. The surgical instrument according to claim 1, wherein the adhesive fluid source includes a time or heat-activated adhesive fluid.

9. An electrosurgical instrument for sealing and/or cutting tissue, comprising:
an end effector assembly including:
 a first jaw member having a plurality of bores defined therein;
 a second jaw member having a plurality of recesses defined therein, at least one of the first or second jaw members movable relative to the other between a first position in which the first and second jaw members are disposed in spaced apart relation relative to one another and a second position in which the first and second jaw members cooperate to grasp tissue therebetween; and
an adhesive applicator assembly including a plurality of first needles operatively mounted in the first jaw member, a plurality of second needles operatively mounted in the second jaw member, and a platform defining an adhesive reservoir in fluid communication with the plurality of first or second needles, the adhesive reservoir containing a pre-determined amount of adhesive fluid therein, at least one of the plurality of first or second needles is movable relative to the first or second jaw members, each of the plurality of second needles defining a bore dimensioned to receive the corresponding plurality of first needles.

10. The surgical instrument according to claim 9, wherein at least one needle of the plurality of first or second needles defines apertures on the sides thereof.

11. The surgical instrument according to claim 9, wherein at least one needle of the plurality of first or second needles defines a plurality of apertures in communication with the adhesive reservoir in the platform such that the adhesive fluid creates a rivet-like adhesive structure on tissue.

12. The surgical instrument according to claim 9, wherein the platform is coupled to a biasing member to bias the platform toward a neutral position in which the plurality of the first needles is disposed within the first jaw member.

13. The surgical instrument according to claim 9, wherein at least one of the first or second jaw members defines a channel extending along a length thereof, the channel configured for reciprocation of a knife blade therein.

14. The surgical instrument according to claim 9, wherein the adhesive fluid includes a time or heat-activated adhesive fluid.

\* \* \* \* \*